United States Patent
Arcelus

Patent Number: 6,149,602
Date of Patent: *Nov. 21, 2000

[54] USER-WORN ELECTROCARDIOGRAM VIEWER DEVICE

[76] Inventor: Almudena Arcelus, 147 Longwood Ave. #2, Brookline, Mass. 02146

[*] Notice: This patent issued on a continued prosecution application filed under 37 CFR 1.53(d), and is subject to the twenty year patent term provisions of 35 U.S.C. 154(a)(2).

[21] Appl. No.: 08/825,828

[22] Filed: Mar. 29, 1997

Related U.S. Application Data

[60] Provisional application No. 60/024,788, Sep. 10, 1996.

[51] Int. Cl.<sup>7</sup> ................................................. A61B 5/0432
[52] U.S. Cl. ........................................... 600/523; 600/509
[58] Field of Search ................................... 600/509, 520, 600/523; 607/32

[56] References Cited

U.S. PATENT DOCUMENTS

| | | | |
|---|---|---|---|
| 4,108,166 | 8/1978 | Schmid | 600/523 |
| 4,120,294 | 10/1978 | Wolfe | 600/523 |
| 4,635,646 | 1/1987 | Gilles et al. | 600/509 |
| 4,791,933 | 12/1988 | Asai et al. | 600/509 |
| 4,809,705 | 3/1989 | Ascher | 600/523 |
| 4,825,874 | 5/1989 | Uhlemann | 600/523 |
| 4,889,134 | 12/1989 | Greenwold et al. | 600/523 |
| 5,003,984 | 4/1991 | Muraki et al. | 600/523 |
| 5,300,093 | 4/1994 | Koestner et al. | 607/32 |
| 5,304,209 | 4/1994 | Adams et al. | 607/32 |
| 5,336,245 | 8/1994 | Adams et al. | 607/32 |
| 5,343,869 | 9/1994 | Pross et al. | 600/523 |
| 5,383,912 | 1/1995 | Cox et al. | 607/32 |
| 5,417,222 | 5/1995 | Dempsey et al. | 600/509 |
| 5,577,510 | 11/1996 | Chittum et al. | 600/523 |
| 5,620,472 | 4/1997 | Rahbari | 607/27 |
| 5,623,926 | 4/1997 | Weiss | 600/509 |
| 5,682,902 | 11/1997 | Herleikson | 600/521 |
| 5,738,104 | 4/1998 | Lo et al. | 600/509 |

Primary Examiner—Kennedy Schaetzle
Attorney, Agent, or Firm—Fish & Richardson, P.C.

[57] ABSTRACT

A user-worn electrocardiogram viewer acquires data relating to a user's electrocardiogram signal. The viewer receives the electrocardiogram signal (by wired or wireless link) and displays it on a self-contained display screen (10). The viewer provides switches (12, 14, 16) operated by the user to adjust the display and processing of the electrocardiogram signal through the selection of parameters such as size of the electrocardiogram signal to be displayed, bandwidth of the electrocardiogram signal to be processed, and speed of the electrocardiogram signal when displayed through the screen. The viewer also includes a storage capability to store the electrocardiogram signal for later recall and analysis. The viewer also includes an infrared port (50) to communicate with the serial port of other devices. The viewer provides other support functions to the user such as display of heart rate, visual display of QRS-detection, and time and date information. The viewer also provides the user with the capability to set a heart rate target zone and heart rate trend. The viewer is easy to operate by the user and suitable for attachment (38, 40) to the user's upper limb, preferably the wrist.

20 Claims, 11 Drawing Sheets

USER-WORN ELECTROCARDIOGRAM VIEWER DEVICE

This application claims benefit of Provisional Appln. 60/024,788 filed Sep. 10, 1996.

BACKGROUND—FIELD OF INVENTION

This invention relates to equipment for displaying the electrical activity of the heart in a living body, and particularly to a portable electrocardiogram viewer worn by the user.

BACKGROUND—DESCRIPTION OF PRIOR ART

Many portable devices have been described before that detect the electrical activity of the heart (henceforth electrocardiogram signal). Many of them allow the user to see only a numeric of the heart rate computed from the detected electrocardiogram signal. Others may include a display of the actual electrocardiogram signal but do so in a very limited way: either for brief and limited periods of time or only for the convenience and use of the examiner and not the user. Furthermore, such devices do not allow the user unrestricted activity; therefore, they are not suitable for long term view of his/her electrocardiogram signal.

Prior Art That Shows Only A Numeric of Heart Rate

Righter et al (in U.S. Pat. No. 4,938,228) describe a wrist-watch device capable of detecting and transmitting an electrocardiogram signal but not displaying it to the user. The device is intended to transmit the electrocardiogram signal via telephone to medical personnel on a remote location. Similar aspects are described in subsequent patents of the same inventor (U.S. Pat. Nos. 5,191,891; 5,226,425; and 5,365,935).

Mills et al (in U.S. Pat. No. 5,289,824) describe another wrist-watch device capable of detecting and transmitting an electrocardiogram signal. The device is intended to transmit the electrocardiogram signal via telephone to medical personnel on a remote location. Similar aspects are described in subsequent patents of the same inventors (U.S. Pat. Nos. 5,317,269; 5,333,616; and 5,351,695).

The devices described above are not intended nor are capable of displaying a continuous, real time electrocardiogram signal. Their purpose is to facilitate the acquisition and transmission of an electrocardiogram signal while providing the user with an indication of heart rate.

Prior Art That Displays the Electrocardiogram Signal for the Convenience and Use of the Examiner or for Brief and Limited Periods of Time Geddes et al (in U.S. Pat. No. 4,606,352) describe a hand-held electrocardiogram monitor to be placed against the chest of a patient by placing and holding the monitor with one hand, on the chest of the patients while performing the reading of the electrocardiogram signal. This monitor is designed to be used by medical personnel in relation to medical emergencies and used for brief periods of time only. The user cannot see his/her electrocardiogram signal because the display is facing away from the user. In addition, the device will not be able to remain in position for long because it requires active support from the examiner to stay in place.

Suzuki (in U.S. Pat. Nos. 5,002,062 and 4,974,599) describes other hand-held portable electrocardiogram monitors to be used by a physician or technician to perform a quick examination of the patient's heart or as an event recorder to be carried by the user during certain activities. These designs emphasize the use of a touch screen to facilitate operator interaction and a memory card for pre-programmed functions and event recording. These designs are not intended for continuous view of the electrocardiogram signal by the user.

Allain (in U.S. Pat. Nos. 5,002,064 and 5,029,590) describes a pocket-size monitor for electrocardiogram signal or electroencephalogram monitoring. This monitor is assumed to be carried in the hand by medical personnel or placed in an adjacent table while performing the reading. It is not designed to be operational while the patients engages in physical activity. This monitor is designed to be used by medical personnel. The design includes the use of electrodes attached to the device in such a way that the user cannot see his/her own electrocardiogram signal.

Platt et al (in U.S. Pat. No. 5,123,419) describe a hand-held device suitable for electrocardiogram signal evaluation including pacemaker activity. This monitor is assumed to be carried in the hand by medical personnel or placed in an adjacent table while performing the reading. This monitor is not designed to be used or worn by the user.

Fujii (in U.S. Pat. No. 5,213,107) describes a portable electrocardiogram monitor to be used by a physician or technician as an event recorder to be carried by the user during certain activities. The primary goal of this design is to reduce battery consumption. In order to better accomplish that goal, the device allows the health care provider to either acquire electrocardiogram signals from the patient or to display a previously stored electrocardiogram signal but not both simultaneously. The device is intended as an event recorder and not for continuous view of the electrocardiogram signal by the user.

None of the above devices will actually facilitate to the user to see and evaluate his/her own electrocardiogram signal because they are primarily designed to be used by a medical/health care professional rather than by the user him/herself. These patented designs are intended to be evaluation aids under certain medical circumstances. Furthermore, they also share the disadvantage that are not designed to be used for extended periods of time. As a result, their shape, size, or mode of use make them difficult or impossible to simultaneously wear and operate by the user.

OBJECTS AND ADVANTAGES

The present invention entirely focuses on the concept that the user wants to see his/her own cardiac activity without the need for any health-care professional. This is a radical departure from all prior art. This departure produces a design that opens up new and unexpected possibilities. As will be later described in the embodiments and claims, the user can now track his/her electrocardiogram signal from several sources (wired or wireless); for the first time an athlete can perform his/her activity while being able to constantly monitor his/her electrocardiogram signal; or a patient with an implantable device (e.g., pacemaker with telemetry capability) can now see his/her electrocardiogram signal at will. These and other new uses cannot be handled by the limitations found in the prior art.

Hence, the present invention solves the aforementioned limitations and presents the user with a convenient (easy to operate, easy to wear) and continuous, real time display of his/her electrocardiogram signal, while at the same time allowing the user unrestricted activity.

Accordingly, one object and advantage of the invention is to provide an electrocardiogram signal display. Other objects and advantages are to provide such a display in a continuous, real time and clearly visible manner. Further objects and advantages are to provide a display that is easily worn and operated by the user with minimal interference with his/her activities.

This invention may prove extremely valuable for individuals who want to have an active lifestyle but are not sure about the state of their cardiac activity and want to monitor it: from athletes in training to persons suffering from cardiovascular disease to persons with implantable devices. The invention may also prove helpful when teaching about cardiac physiology.

Still further objects and advantages will become apparent from a consideration of the ensuing description and accompanying drawings.

REFERENCE NUMERALS IN DRAWINGS

| | |
|---|---|
| 10 | display |
| 12 | left switch |
| 14 | center switch |
| 16 | right switch |
| 18 | housing |
| 26 | input protection circuit |
| 28 | electrode cable |
| 30 | instrumentation amplifier circuit |
| 32 | microcontroller |
| 34 | power supply |
| 38 | upper edge strap |
| 40 | bottom edge strap |
| 42 | signal conditioning stage |
| 44 | electrodes |
| 46 | on/off switch |
| 50 | infrared port |
| 52 | chest belt |
| 54 | FM transmitter |
| 56 | FM receiver |
| 58 | non-volatile memory |
| 60 | dry electrodes |

SUMMARY OF THE INVENTION

The invention is a portable electronic device with a clearly readable display that can be easily operated and worn by the user in a variety of medical and non-medical situations. The device detects (wired mode) or receives (wireless mode) the electrocardiogram signal of the user, amplifies, filters, and converts it to a digital representation suitable for display and storage. The device provides switches, operated by the user, to adjust the display and processing of the electrocardiogram signal through the selection of parameters such as size of the electrocardiogram signal to be displayed, bandwidth of the electrocardiogram signal to be processed, and the speed of the electrocardiogram signal when displayed through the screen. The device also includes a storage capability to store the electrocardiogram signal for later recall and analysis. The device also includes an infrared port to communicate with the serial port of other devices. The device provides other support functions to the user such as display of heart rate, visual display of QRS-detection, and time and date information. The device also provides the user with the capability to set a heart rate target zone and heart rate trend. The device is easy to operate by the user and suitable for attachment to the user's upper limb, preferably the wrist.

Figure 1:
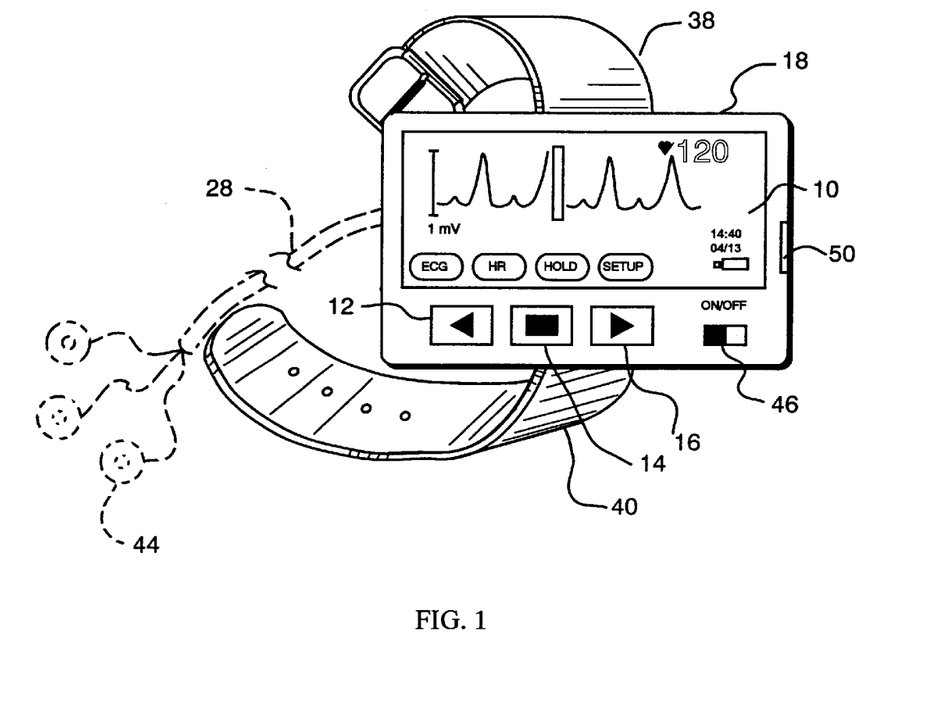
FIG. 1 shows an external view of the preferred embodiment of the invention.
Figure 2:
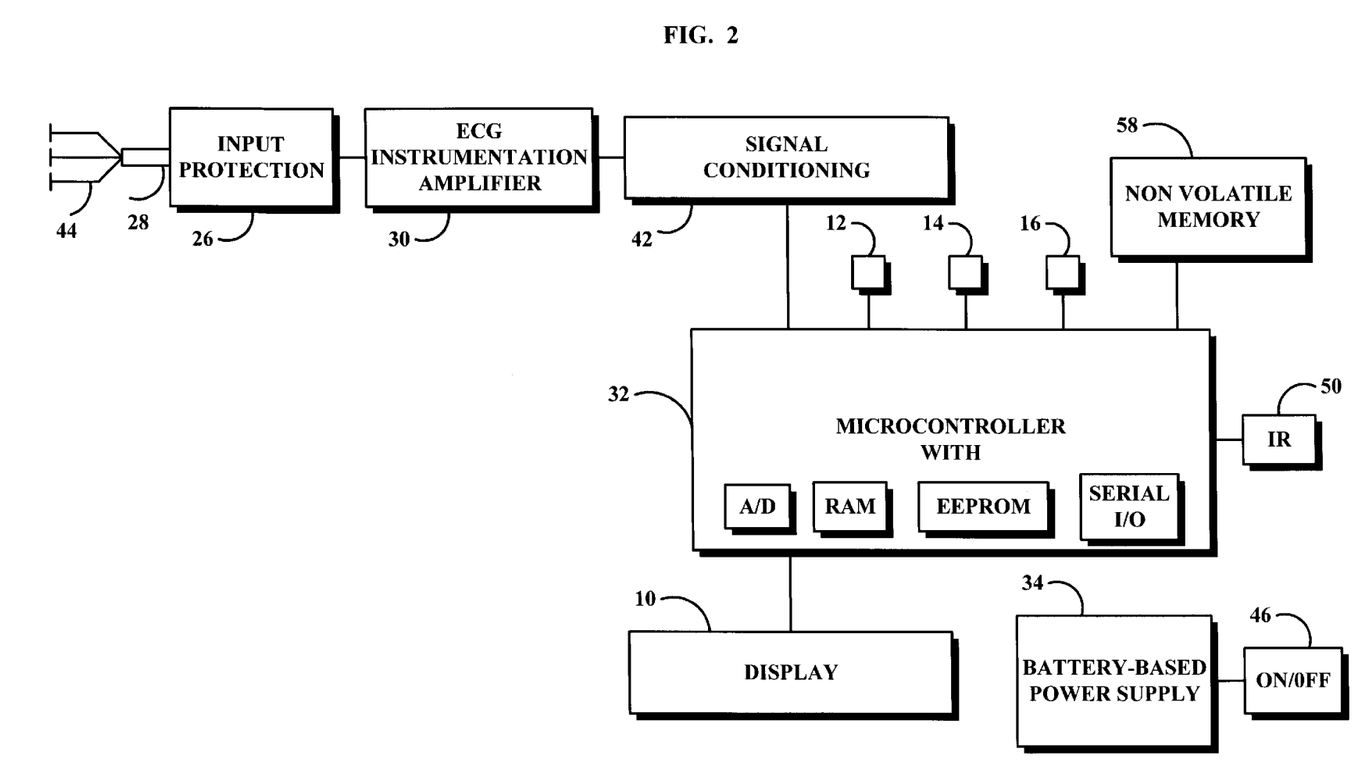
FIG. 2 shows the block diagram of the electronic components of the preferred embodiment of the invention.

DESCRIPTION—MAIN EMBODIMENT—FIGS. 1, 2

FIG. 1 shows the external (user) view of the invention. The invention is an electronic device with a flat display 10 enclosed by a plastic housing 18. There are four switches in the lower part of the assembly: left switch 12, center switch 14, right switch 16, and on/off switch 46. The electrode cable 28 attaches to the left side of the assembly by a connector (not shown) and to two or three electrodes 44 on the other end. There are two flexible plastic straps attached to the assembly, an upper edge strap 38 and a bottom edge strap 40. There is also an infrared port 50 on the right side of the housing.

FIG. 2 illustrates the functional blocks of the electronic components of the present invention. The invention has an electrode cable 28 attached through a connector, followed by an input protection circuit 26 and an electrocardiogram signal instrumentation amplifier 30. Next, there is a signal conditioning stage 42 connected to the microcontroller 32 unit. Also connected to the microcontroller 32 are a liquid crystal display 10; three switches: left switch 12, center switch 14, and right switch 16; an infrared port 50; and additional non-volatile memory 58. Finally, there is a battery based power supply 34 circuit with an on/off switch 46.

OPERATION—MAIN EMBODIMENT—FIG. 1

The invention is a portable electronic device, battery operated, with a clearly readable display that can be easily worn by the user or attached to a nearby object (e.g. a bicycle frame). The essential operation of the device is to acquire the electrocardiogram signal from the user or patient and conveniently display it within easy reach of the user.

The operation of the device requires that the user attaches either two or three electrodes 44 to the his/her skin in any of the conventional electrode positions or other electrode positions. The user then connects those electrodes to the electrode cable 28 which in turn is connected to the housing 18. Finally, the user finds a position where to attach the housing 18 to his/her body or a nearby object. Normally, the left or right arm or wrist is a suitable place. Other places may be possible, e.g., the waist, a nearby table, a bicycle frame, or a treadmill frame. With the device properly connected and attached, the user is able to see his/her electrocardiogram signal in a continuous manner.

The device automatically calculates and displays the heart rate (the number of beats per minute), displaying a small symbol (e.g., a heart) every time a beat is detected. Other functionality may include functions related to the electrocardiogram such as heart rate trends or convenience functions such as the time of day, the date, and low battery indication.

Hardware Operation—FIG. 2

FIG. 2 refers to the operation of the electronic components. The electrocardiogram signal is sensed by either two or three electrodes 44 attached to the skin of the user or patient. Normally, two electrodes are sufficient to pick up the electrocardiogram signal. The use of the third electrode is recommended to reduce power line noise in some environments. In addition, this third electrode increases the range of electrode positions available (e.g., modified chest leads). The electrode cable 28 receives the electrocardiogram signal from the electrodes 44 and sends it to the input protection circuit 26. This input protection circuit provides high-voltage protection (e.g., defibrillation shock). The electrocardiogram signal then continues to the instrumentation amplifier 30 that consists of a conventional configuration with three operational amplifiers. The gain at this stage is 8.

Next is the signal conditioning stage 42 that consists of (1) a single pole low-pass filter with frequency cutoff at 20, 40, or 125 Hz; (2) a single pole high-pass filter with frequency cutoff at 0.05 or 0.5 Hz; (3) a variable gain of 65.5, 125, 250, or 400 for an overall gain of 500, 1000, 2000, or 4000 respectively; and (4) an additional single pole high-pass filter with frequency cutoff at 3.5 Hz. This filter will be used only for brief periods for the purpose of controlling the sudden baseline deviations that sometimes occur during normal operation. The microcontroller 32 controls the cutoff frequencies of the filters and the gain using analog switches. The output of the signal conditioning stage 42 is connected to the analog-to-digital port and other control pins of the microcontroller 32.

The microcontroller is also connected to the liquid crystal display 10, three switches 12, 14, 16, and to the circuitry needed by the microcontroller such as a crystal oscillator (not shown) and contrast control for the display (not shown). The microcontroller 32 has an internal analog-to-digital conversion capability, RAM and EEPROM memories, and a serial port for communication with other devices. Non-volatile memory 58 with a capacity of 2 Kbytes, is connected to the microcontroller 32 to allow for storage of user settings and electrocardiogram signal segments. The serial output of the microcontroller 32 is connected to the infrared port 50 that allows the device to communicate with outside devices while maintaining complete isolation for the user. The battery-based power supply 34 that provides power to all the circuits has a reset circuit to reset the microcontroller 32, a voltage regulator (not shown), and an on/off switch 46.

Software Operation—FIGS. 2, 7A, 7B, 8, 9A, 9B

The microcontroller 32 has programming instructions (software) to coordinate all the functions of the device. The software includes the analog-to-digital conversion of the electrocardiogram signal, typically, with 8 bits of resolution at 500 samples per second. The code includes instructions to present the data acquired to the liquid crystal display, to detect the QRS component of the electrocardiogram signal, and to calculate the heart rate. In addition, the software allows the user to modify the operation of the device via the use of switches 12, 14, and 16.

The software consists of the following three routines: the main routine, the interrupt routine, and the QRS detector routine. Once the user has turned the device on, the main routine starts running indefinitely, only to be briefly interrupted by the interrupt routine that receives a sample of the electrocardiogram signal and processes it through a digital notch filter and the QRS detector routine. Once the interrupt routine completes its tasks, the main routine resumes operation until the next interrupt takes effect.

Figure 7A:
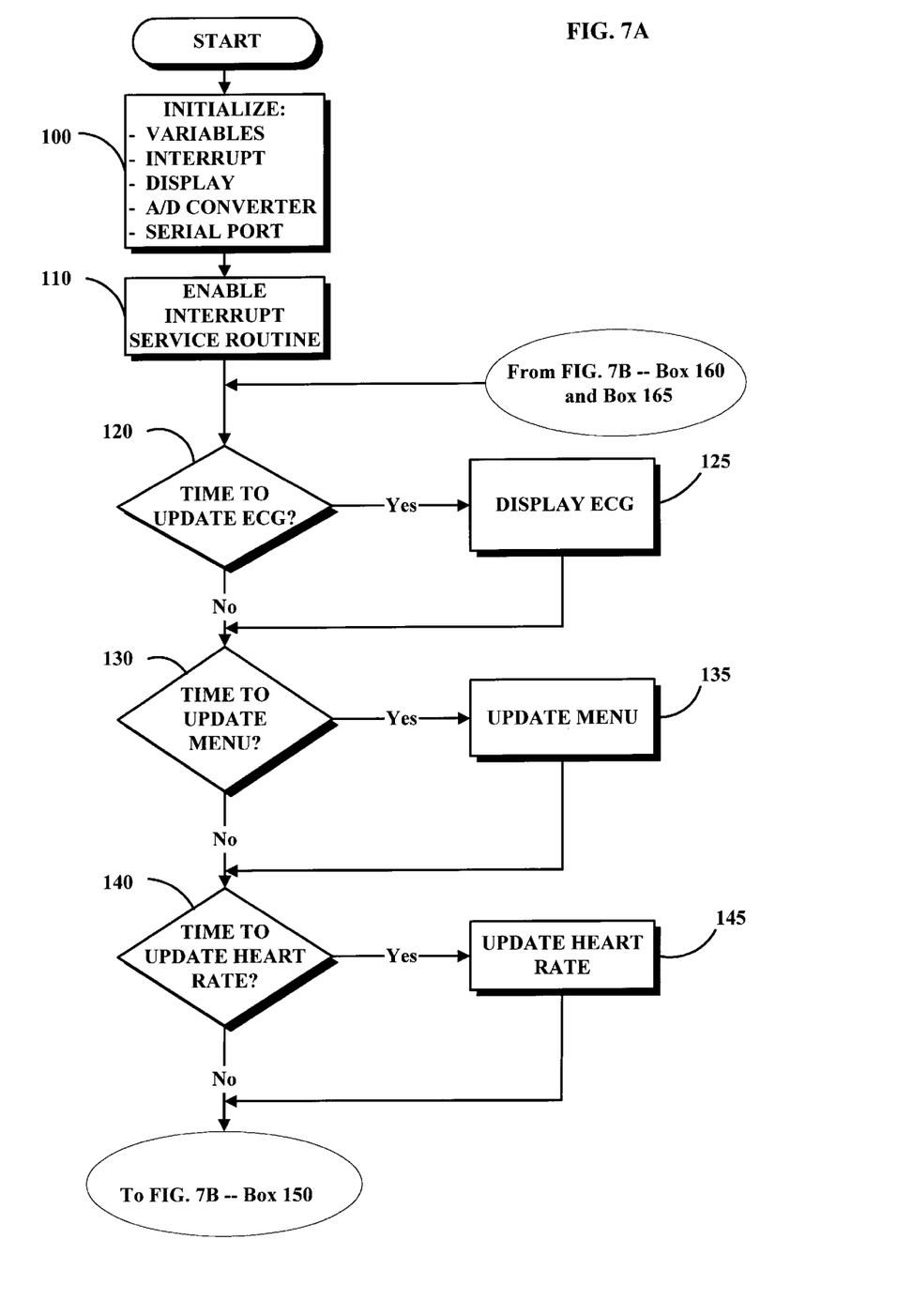
FIGS. 7A and 7B show the flowchart for the main software routine of the preferred embodiment of the invention.
Figure 7B:
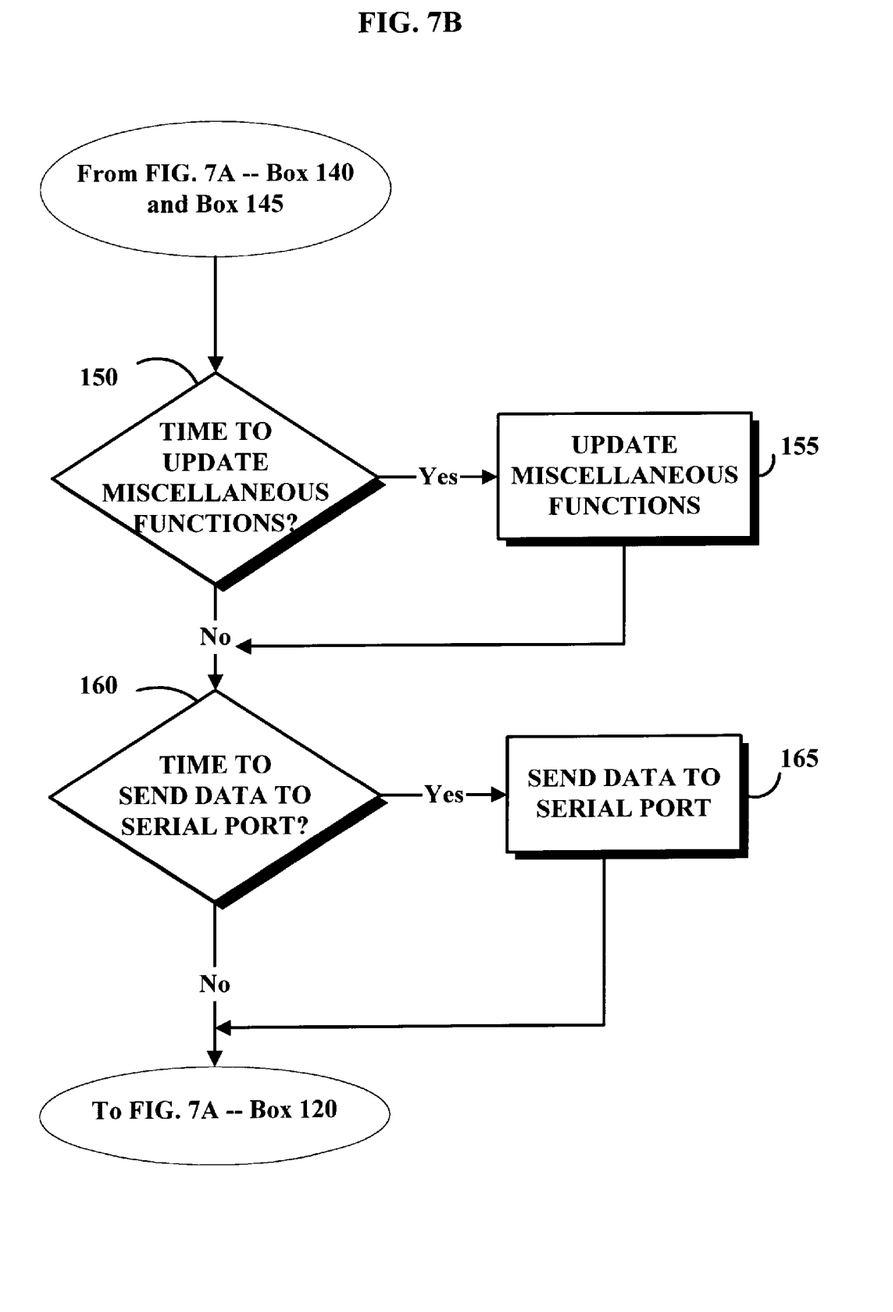

Main Routine—FIGS. 7A, 7B

The main routine initializes the device, updates all items on the display, and sends data through the serial link when needed. FIGS. 7A and 7B depict a flowchart of the main routine. Block 100 initializes all the global variables, the timers, the display, the A/D port, the serial port, and the interrupt service routine during the start up of the device. Block 110 enables the interrupt routine (described below). Block 120 checks one of the timers to check if it is time to update the electrocardiogram signal on the display. Block 125 updates the display with the latest electrocardiogram data with the desired sweep speed (12.5, 25, or 50 mm/sec).

Block 130 checks for the flags associated with the user switches. These flags are set in the interrupt routine. Block 135 displays the appropriate selection. Block 140 checks for a new value of heart rate. Block 145 displays the heart rate at the upper right hand corner of the display. Block 150 keeps track of the calibration and battery charge and allows Block 155 to update them. Finally, Block 160 checks for a request to send data through the serial port and Block 165 transfers the data to it.

Figure 8:
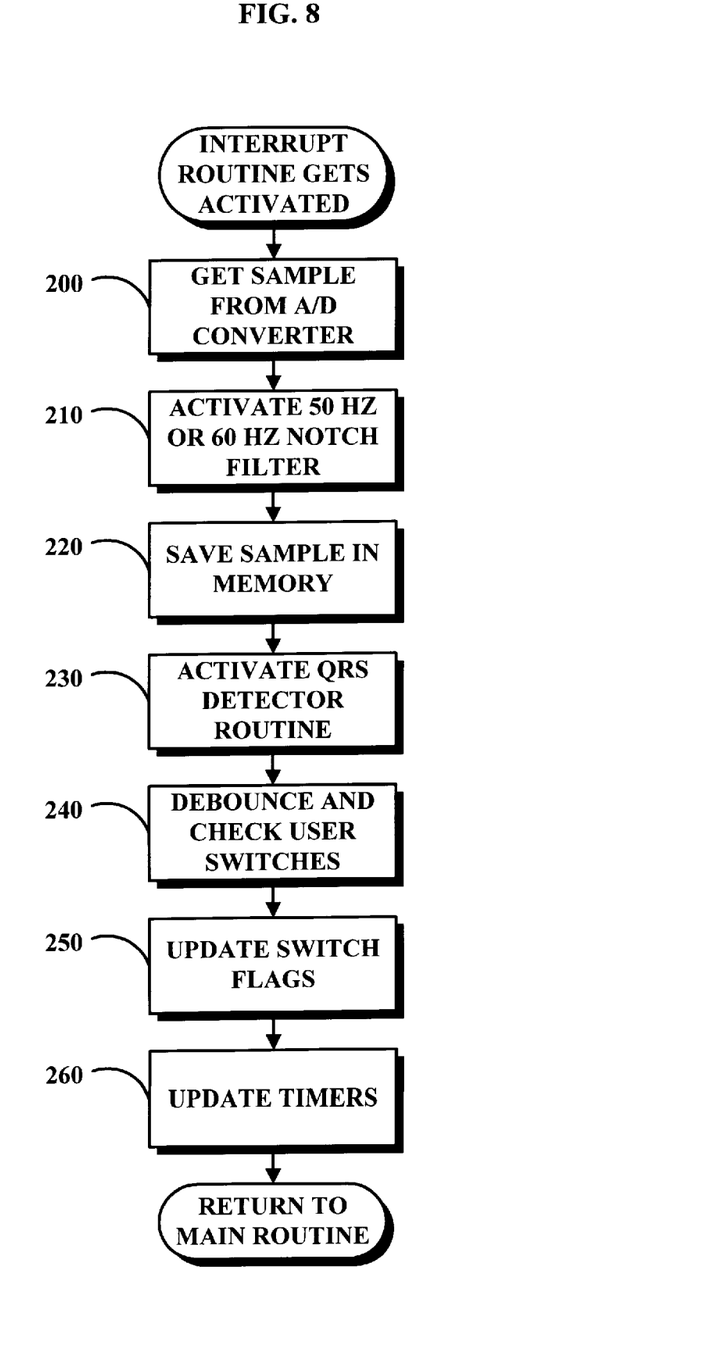
FIG. 8 shows the flowchart for the interrupt service routine of the preferred embodiment of the invention.

Interrupt Routine—FIG. 8

The interrupt routine samples the electrocardiogram signal, performs additional filtering (50 or 60 Hz), runs the QRS detector routine, updates timers, and polls the user switches. Control flags and timers updated by the interrupt routine are used by the main routine to update the display. FIG. 8 shows a block diagram describing the interrupt routine. Block 200 gets a sample of electrocardiogram signal every 2 msec. The sample is filtered by a notch filter (Block 210) at either 50 Hz or 60 Hz. The filtered electrocardiogram sample is stored in memory by Block 220. Block 230 is the QRS detector routine (described below). Block 230 detects the R waves in the electrocardiogram signal and calculates heart rate from them. Block 240 debounces and checks the user switches. Block 250 updates all the flags associated with the state of the switches. Finally, Block 260 updates the timers.

Figure 9A:
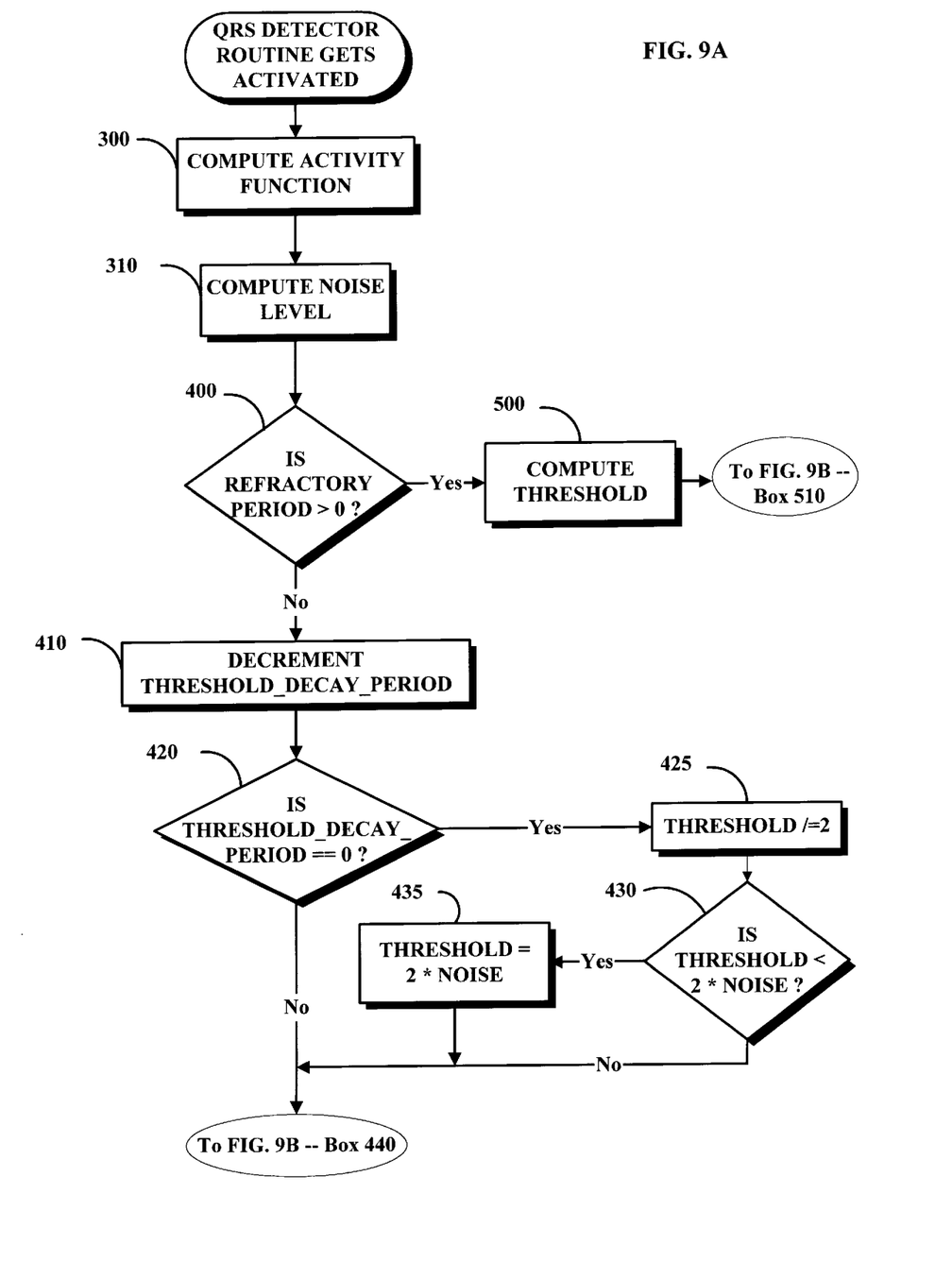
FIGS. 9A and 9B show the flowchart for the QRS detector used in detecting the R waves and calculating heart rate in the preferred embodiment of the invention.
Figure 9B:
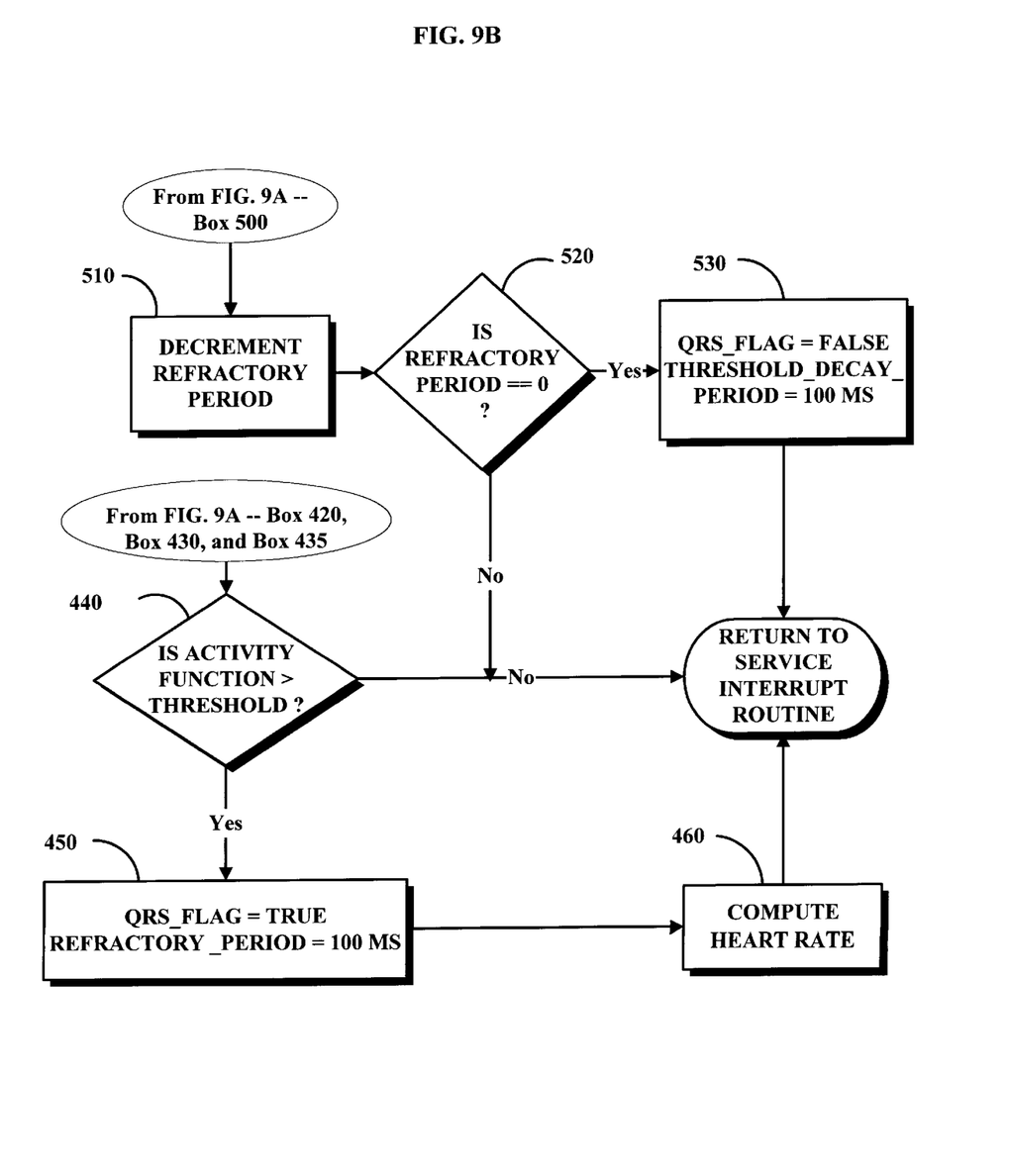

QRS Detector Routine—FIGS. 9A, 9B

The QRS detector finds the R-waves in the electrocardiogram signal and calculates the heart rate from them (Sun, Y. et. al., "Microcontroller-Based Real-Time QRS Detection," *Biomedical Instrumentation and Technology* 1992; 26:477–484). This QRS detector routine is activated through the interrupt routine and returns the processed information to the interrupt routine to be displayed. Referring to FIGS. 9A and 9B, Block 300 computes an activity function based on the first-order backward difference d[n]. If s[n] denotes the current ECG sample, then d[n]=s[n]−s[n−1] denotes the first-order backward difference. The activity function is computed as follows: AF[n]=d[n]×d[n−1]×d[n−2] if d[n], d[n−1], and d[n−2] have the same sign, otherwise AF[n]=0. Block 310 computes the noise level of the signal. Block 310 is designed to prevent the threshold to become too low.

There is a refractory period (100 ms) after each detection to avoid multiple detections. Block 400 checks if the signal is within that period. If so, Block 500 sets a threshold at the maximum of AF[n] during the refractory period (this refractory period includes the recently detected QRS). Block 510 decrements the refractory period. Block 520 checks to see if the refractory period has expired. If so, Block 530 sets a QRS flag to false and resets the threshold decay period to 100 ms. If Block 400 determines that the signal is not in the refractory period then Block 410 decrements the threshold decay period. When a fixed time period elapses (Block 420), the threshold is reduced by half (Block 425). The threshold, however, is not allowed to go below a minimum level, which is two times the noise level of the signal (Blocks 430 and 435).

Block 440 checks if the activity function is greater than the threshold, if so a new QRS wave has been recognized. Block 450 then sets the QRS flag to true and resets the refractory period to 100 ms. Finally, Block 460 computes the heart rate based on the last four QRS detected.

User Controls—FIG. 1

The device includes four switches that allow the user to control the operation of the device. These four switches are shown in FIG. 1.

On/Off—turns power on or off to the device.

The following three switches allow the user to operate the menu buttons that appear at the bottom of the display ("ECG", "HR", "HOLD", and "SETUP"):

Left Switch—moves the focus to the menu button to the left of the currently selected (highlighted) menu button.

Center Switch—activates the currently selected (highlighted) menu button.

Right Switch—moves the focus to the menu button to the right of the currently selected (highlighted) menu button.

Display Indicators—FIG. 1

All the indicators are shown on different regions of the display. An example of the display layout can be seen in FIG. 1.

Heart Rate—Average heart rate is computed on the last 4 RR intervals, and is updated only when the new value is different from the currently displayed value. The heart rate is shown as a numeric on the upper right hand corner of the display. The units are in beats per minute.

QRS Plop—A small figure visually indicates that a QRS has been detected. This plop is updated every beat, and shown as a blinking heart to the left of the heart rate numeric.

Hour—The hour in HH:MM format is updated every minute, and is shown at the lower right hand corner of the display.

Date—The date in MM/DD format is updated every day, and is shown below the hour numeric.

Low Battery—The small battery figure is displayed at lower right hand corner of the display when the battery reaches a critically low voltage.

Input/Output Communications—FIG. 1

This device receives the electrocardiogram signal through the user cable and has the capability of transmitting the processed electrocardiogram signal through an infrared port.

User cable—The invention accepts cables with two or with three electrodes. The electrodes 44 are placed preferably on the chest of the user and attached to one end of the cable. The other end of the cable connects to the housing 18. Configurations with other cables that can handle more electrodes are also possible.

Infrared Link—This infrared port 50 allows the device to have serial communication with other external devices with infrared serial ports. A special cable is provided (not shown) to connect to the serial port of devices without infrared capability. Isolation from the power line is maintained in all cases.

Menu Selection—FIG. 1

Three switches or pushbuttons are provided to select from a number of functions that enhance the operation of the device. The three switches 12, 14, 16 allow the user to scroll left, to scroll right, or to select from a menu of choices located on the bottom of the display 10. The four menu functions are "ECG," "HOLD," "HR," and "SETUP." These functions are shown as boxes on the lower part of the display 10. Selecting any one of them displays a sub-menu, and each sub-menu in turn offers several selections that can be activated when pressing the center switch 14. The description of the menu structure is as follows:

ECG Menu

| Submenu | Selections |
|---|---|
| Size | 5, 10, 20, 40 |
| Filter | monitoring, exercise, diagnostic |
| Speed | 12.5, 25, 50 |
| Back | |

"Size" allows the user to increase or decrease the size of the electrocardiogram signal by the required amount (the units are in mm/mV). "Filter" allows the user to select three different filters for three correspondingly different bandwidths: exercise (0.5–20 Hz), monitoring (0.5–40 Hz), and diagnostic (0.05–125 Hz). "Speed" allows the user to change how fast the electrocardiogram signal moves from left to right on the display (the units are in mm/sec). "Back" moves the user back to the previous level. The default values are for "Size": 10, "Filter": monitoring; and "Speed": 25.

HR Menu

| Submenu | Selections |
|---|---|
| Upper | inc, dec |
| Lower | inc, dec |
| Trend | 5, 15, 60 |
| Back | |

This menu allows the user to set the target zone for heart rate. "Upper" sets an upper limit for heart rate in beats per minute and "Lower" sets a lower limit for heart rate in beats per minute. The user can use the "inc" and "dec" selections to increase or decrease the limits in one beat per minute increments. "Trend" graphically displays the heart rate every 5, 15, or 60 seconds for up to 1, 4 or 12 hours respectively. "Back" moves the user back to the previous level. The default values are for: "Upper": 150, "Lower": 100, and "Trend": 15.

HOLD Menu

| Submenu | Selections |
|---|---|
| Protect | |
| Send | |
| Recall | 1, 2, 3, 4, 5 |
| Back | |

When "Hold" is pressed, the display freezes the current electrocardiogram signal and the sub-menu is shown. "Protect" allows the user to save the last 6 seconds segment of electrocardiogram signal and does not overwrite the segment (unless "Protect" is pressed again when displaying the same segment). Up to 5 different segments of 6 seconds duration each can be protected (saved). "Send" allows the user to send the current segment through the infrared port 50. "Recall" allows the user to review a previously stored segment. "Back" moves the user back to the previous level.

SETUP Menu

| Submenu | Selections |
|---|---|
| Hour | 0, 1, 2, . . ., 23 |
| Min | 0, 1, 2, . . ., 59 |
| Month | 1, 2, 3, . . ., 12 |
| Day | 1, 2, 3, . . ., 31 |
| Contrast | inc, dec |
| Notch Filter | 50, 60 |
| Back | |

"Hour" and "Min" allow the user to set the time. "Month" and "Day" allow the user to set the date. "Contrast" allows the user to adjust the contrast level for the liquid crystal display 10. "Notch Filter" selects a 50 or 60 Hz notch filter to reduce the power line interference. The default values are for: "Hour": 12, "Min": 0, "Month": 1, "Day": 1, "Contrast": (medium brightness), "Notch Filter": 60.

All the settings are stored in non-volatile memory such that they will be saved before power is off and restored when powers is on again.

Figure 3:
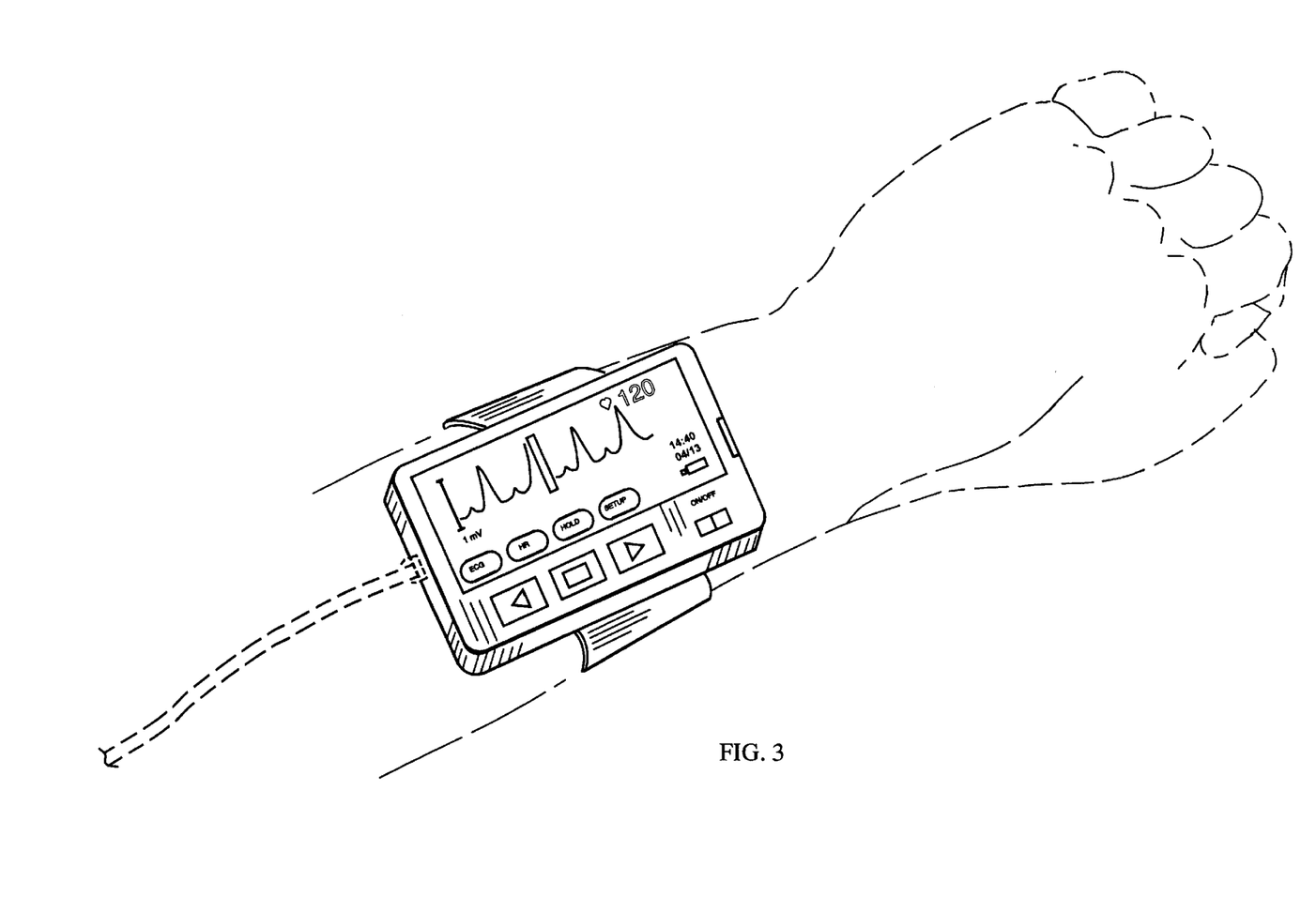
FIG. 3 shows an example of use of the preferred embodiment.

Uses of the Invention—FIGS. 1, 3

FIG. 3 shows a typical use of the present invention. The user wears the invention preferably on her wrist, allowing her to see her electrocardiogram signal. Note that in this example the user has a cable that connects the device to three electrodes placed on the skin of the user. At other times, the cable may not be needed when there is an electrocardiogram signal being transmitted by an implantable device or by other device sensing the surface electrocardiogram signal (e.g., chest belt).

Uses perfectly suited for this invention are: (1) The user can engage in her daily activities and at the same time observe her electrocardiogram signal. (2) The user can exercise in a stationary apparatus (e.g., a bicycle or a treadmill) and monitor her cardiac activity at the same time. The user can attach the electrocardiogram viewer to her left arm or to a stationary part of the apparatus while still connected to it by the electrode cable 28. (3) A user with an implantable pacemaker with telemetry transmission of the electrocardiogram signal may be interested in observing her own electrocardiogram signal during her daily activities and even save some electrocardiogram signal segments for later recall or analysis. (4) A patient with an implantable cardioverter-defibrillator device can save the electrocardiogram signal before and after a cardioversion episode. (5) Teachers and students interested in the principles of cardiac electrophysiology can easily learn from live or simulated electrocardiogram signals being readily displayed by the viewer. (6) Any other daily, exercise, or medical situation that may benefit from observation of the electrocardiogram signal in real time and without disrupting the activities of the user.

Figure 4:
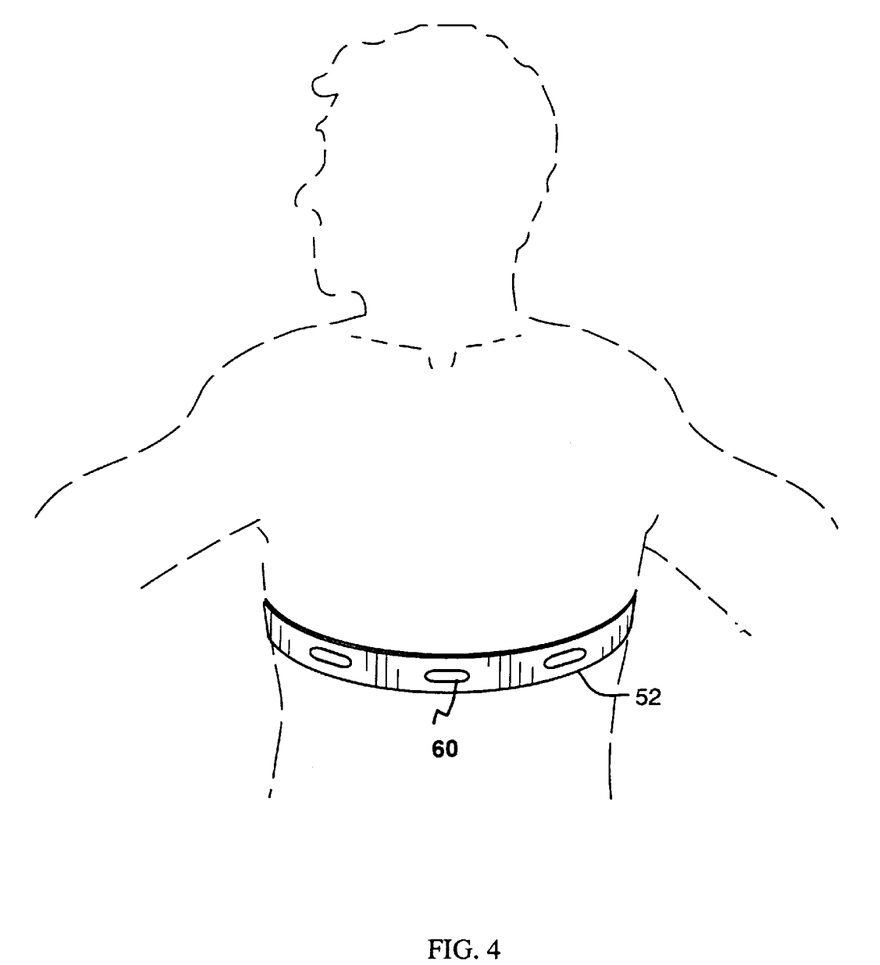
FIG. 4 shows the external view of the chest belt with transmitter unit used in other embodiment of the invention.
Figure 5:
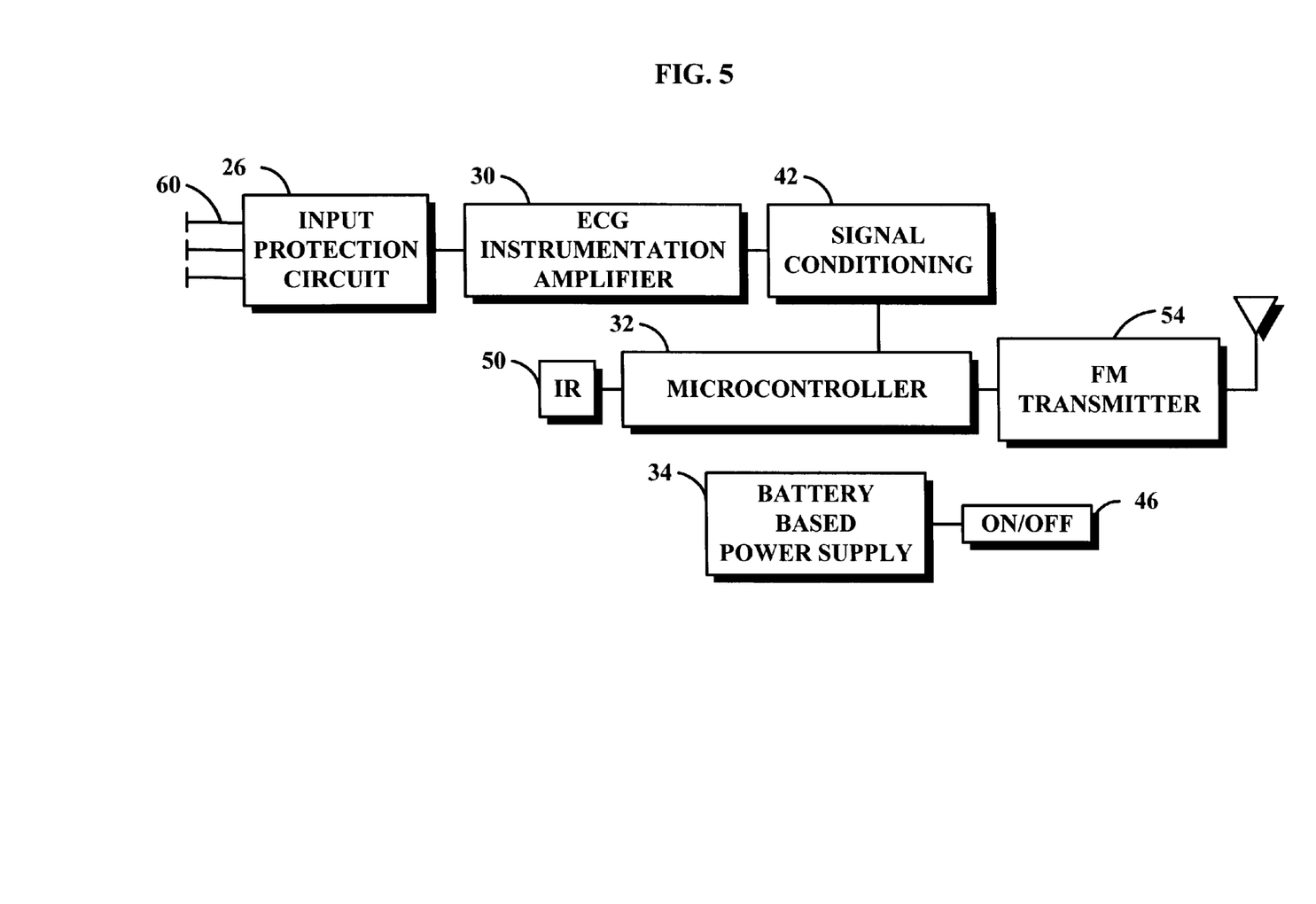
FIG. 5 shows the block diagram of the electronic components contained in the chest belt (transmitter unit) of other embodiment of the invention.
Figure 6:
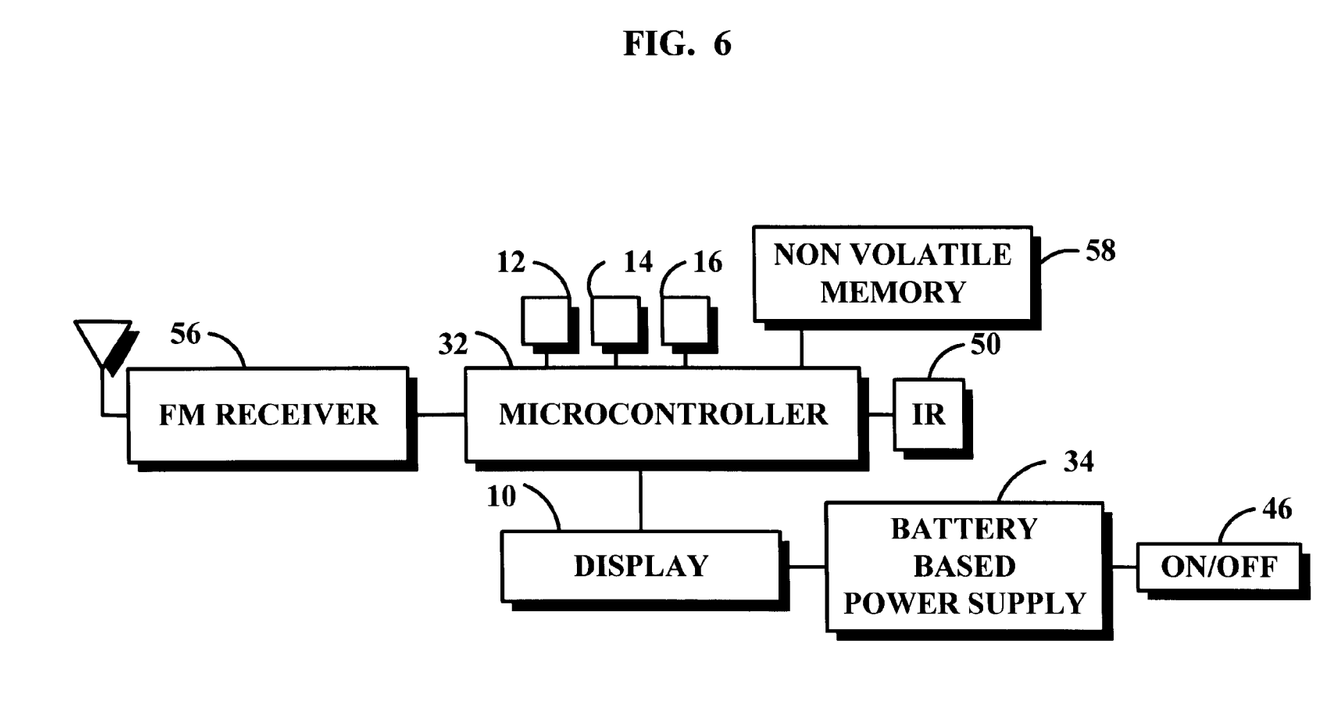
FIG. 6 shows the block diagram of the electronic components contained in the viewer portion (receiver unit) of other embodiment of the invention.

DESCRIPTION—ALTERNATIVE EMBODIMENTS—FIGS. 4, 5, 6

This embodiment is similar to the main embodiment except that instead of using electrode cables to send the electrocardiogram signal from the electrodes to the display, a radio frequency ("RF") link is used. The RF link can have many different implementations: it can be part of an implantable device or it can be mounted on the surface of the skin. An example of the later is described herein whereby the RF link transmits the electrocardiogram signal from electrodes located on the chest of the user to a nearby receiver where the display is (e.g. wrist).

FIG. 4 shows a chest belt 52 attached to the user. This chest belt 52 has three dry electrodes that make contact with the skin of the user. The chest belt also has the electronics to detect, process, and transmit the electrocardiogram signal of the user. The chest belt electronics are all enclosed in a combination of a plastic housing and a stretchable, washable material.

FIG. 5 shows the block diagram of the electronics contained in the chest belt 52. The dry electrodes 60 detect the electrocardiogram signal from the user. These electrodes are connected to an input protection 26 stage, that in turn connects to an instrumentation amplifier 30 followed by signal conditioning stage 42. The signal continues to the microcontroller 32 that then connects to an FM transmitter 54 and to an infrared port 50. The chest belt is powered by a battery based power supply 34 with an on/off switch 46. The electronics of this transmitter unit have most of the elements in the preferred embodiment shown in FIG. 2. The difference here is that there is an FM transmitter 54 instead of the display, user switches, and electrode cable.

FIG. 6 shows the functional blocks of the receiver unit. The receiver unit has an FM receiver 56; a microcontroller 32; a display 10; three switches: left switch 12, center switch 14, and right switch 16; an infrared port 50; a battery based power supply 34 with an on/off switch 46; and non-volatile memory 58.

OPERATION—ALTERNATIVE EMBODIMENTS—FIGS. 5, 6

The electrocardiogram signal is detected, amplified, filtered, and transmitted by the transmitter unit. The transmitted signal is then received by the receiver unit. The receiver unit performs the display of the electrocardiogram, the user setup, and the storage functions in manner similar to the preferred embodiment.

The operation is very similar to the operation described in the main embodiment, with the difference that the user positions the transmitter unit in one place (i.e. user chest) and the receiver unit on another nearby place (e.g. user wrist, bicycle frame).

This embodiment allows for greater freedom of movement, but it also restricts the electrode positions to only one, since electrodes can only be placed in fixed positions in the chest belt (or in an implantable device), instead of any arbitrary location as in the main embodiment.

CONCLUSION, RAMIFICATIONS, AND SCOPE

The invention is a portable electronic device with a clearly readable display that can be easily operated and worn by the user in a variety of medical and non-medical situations.

The invention has been described in detail in the preferred embodiment as well as in an alternate embodiment. Although the descriptions above contain many specificities, these should not be construed as limiting the scope of the invention but as merely providing illustrations of some of the presently preferred embodiments of this invention. Various other embodiments and ramifications are possible within its scope. For example: (1) A pacemaker detection circuit that includes a high pass filter with cutoff at 1500 Hz, a rectifier, and a comparator with variable threshold. The pacemaker detection circuit generates an output pulse whose rising edge produces an interrupt in the microcontroller 32 every time that there is a pacemaker pulse in the electrocardiogram signal. This circuit will enhance the operation of the invention for users with implanted artificial pacemakers. (2) Another modification may include the use of a miniature speaker to produce tones for different aspects of the operation of the device (e.g., every time there is a QRS detection). (3) Another modification may allow for the use of a 10 electrode cable for detection of the 12-lead electrocardiogram. (4) Another modification may include large amounts of non-volatile memory for long term storage of the electrocardiogram signal. (5) Another modification may include the use of dry electrodes attached to the main housing. (6) Another modification may include circuitry necessary for the detection and processing of other physiological parameters (e.g., temperature).

Thus the scope of the invention should be determined by the appended claims and their legal equivalents, rather than by the examples given.

What is claimed is:

1. A portable, customizable user-worn electrocardiogram device for heartbeat waveform monitoring comprising:
   a portable housing having a predetermined size and shape so as to be worn on a body limb of a user;
   user controllable switches that allow interactive control of the device by the user;
   an electronic system contained in the housing to produce a visual representation of a QRS electrocardiogram waveform, said system comprising:
   a signal port that is provided to receive a electrocardiogram signal from external electrodes that are not part of the housing;
   a processor responsive to the electrocardiogram signal to process the electrocardiogram signal in real time;
   an analog-to-digital converter coupled between the signal port and the processor;
   a memory to store a program to control the processor, said stored program including instructions that cause the processor to:
   activate menu features of the device to allow customized configuring of the device in accordance with signals fed to the processor from the user selectable switches; and,
   select a filter response from a plurality of filter responses to filter the electrocardiogram signal in accordance with an activity characteristic of a user; and
   a display mounted on the portable housing, and responsive to a signal provided from the processor to render the QRS electrocardiogram waveform in real time.

2. The device of claim 1 further including:
   at least one strap to attach said housing to the body limb of the user.

3. The device of claim 1 further comprising:
   at least two external electrodes and wherein the signal port is responsive to signals from the at least two external electrodes that are not part of the housing and which are adaptable to be coupled to the user.

4. The device of claim 3 further comprising:
   at least one r.f. transmitting device;
   and wherein the electrodes are coupled to the r.f. transmitting device and the signal port includes an r.f. receiver and is responsive to an r.f. signal produced from the r.f. transmitting device that transmits the electrocardiogram signal from electrodes coupled to the user.

5. The device of claim 1, wherein said memory further includes instructions that cause the processor to:
   process the electrocardiogram signal to detect an R-wave component of the signal; and
   calculate heartbeat rate from successive occurrences of the R-wave component.

6. The device of claim 1 wherein the user controllable switches are carried by the housing.

7. The portable, customizable user-worn electrocardiogram device of claim 1 wherein the plurality of filter responses in accordance with the activity characteristic of a user include an exercise mode and a monitoring mode.

8. The portable, customizable user-worn electrocardiogram device of claim 7 wherein the plurality of filter responses includes a diagnostic mode.

9. A portable, user-worn electrocardiogram device for heartbeat waveform monitoring comprising:
   a portable housing having a predetermined size and shape so as to be worn on a body limb of a user such that a heartbeat waveform of the user may be viewed by the user during normal activities;
   user controllable switches carried by the housing that allow interactive control of the device by the user;
   a signal port that is provided to receive heartbeat signals received from electrodes external to the electrocardiogram device;
   a signal processing circuit to process the heartbeat signals from external electrodes and to produce digitized samples of the heartbeat signals;
   a processor responsive to the heartbeat signals from the signal port;
   a display mounted on the portable housing, and responsive to digitized samples of the heartbeat signal provided from the processor to render the visual display of a QRS electrocardiogram waveform in real time; and
   a memory storing a computer program comprising instructions for causing the processor to:
   activate menu features of the device to allow customized configuring of the device in accordance with signals fed to the processor from the user selectable switches;
   select a filter response from a plurality of filter responses to filter the electrocardiogram signal in accordance with an activity characteristic of the user;
   determine whether an update of a time interval has occurred and if so, update the display with the electrocardiogram waveform.

10. The device of claim 9 further comprising:

at least two remote electrodes; and wherein the signal port is coupled via cables to the at least two remote electrodes that are not part of the housing and which are adaptable to be coupled to the user.

11. The device of claim 9 further comprising:

an r.f. transmitting device; and wherein the electrodes are coupled to the r.f. transmitting device and the signal port further comprises an r.f. receiver and is responsive to an r.f. signal produced from the r.f. transmitting device that receive heartbeat signals from electrodes coupled to the user.

12. The device of claim 9, wherein said memory further includes instructions that cause the processor to:

process the signals to detect an R-wave component of the signal; and calculate heartbeat rate from successive occurrences of the R-wave component.

13. The device of claim 9, wherein said signal processing circuit comprises:

an amplifier that receives and amplifies the heartbeat signal;

a filter to filter the heartbeat signal from the amplifier; and an analog-to-digital converter responsive to the heartbeat signal from the filter to produce the digitized samples of the heartbeat signal.

14. The device of claim 9 further comprising a communications port that provides a link between the electrocardiogram device and peripheral devices external to the electrocardiogram device.

15. The device of claim 14 wherein the link is an r.f. link.

16. The device of claim 14 wherein the link is an infrared link.

17. A portable, user-worn electrocardiogram device for heartbeat waveform monitoring comprises:

a portable housing having a predetermined size and shape so as to be worn on a body limb of a user such that a heartbeat waveform may be viewed by the user during normal activities;

a signal port to receive heartbeat signals, said signal port comprising:

an r.f. receiver to receive heartbeat signals from an r.f. transmitting device coupled to electrodes that are external to the electrocardiogram device; or a cable connection to receive a cable connecting electrodes that are external to the device;

a signal processing circuit to process the heartbeat signals from the r.f. receiver or the cable connection, and to produce digitized samples of the heartbeat signals, said processing circuit comprising:

an amplifier that receives and amplifies the heartbeat signal;

a filter to filter the heartbeat signal from the amplifier; and an analog-to-digital converter responsive to the heartbeat signal from the filter to produce the digitized samples of the heartbeat signal;

a processor responsive to the digitized samples of the heartbeat signal from the signal port;

a display mounted on the portable housing, and responsive to digitized samples of the heartbeat signal provided from the processor to render the visual display of an electrocardiogram signal in real time;

user controllable switches that allow interactive control of the device by the user, and a memory storing a computer program comprising instructions for causing the processor to:

control the signal port to provide digitized samples of the heartbeat signal to the processor;

determine whether an update of a time interval has occurred and if so, update the display with the electrocardiogram waveform;

process control signals from the switches;

activate menu features of the device in accordance with the control signals from the switches to allow customized configuring of the device in accordance with signals from the user selectable switches; and select a filter response from a plurality of filter responses to filter the electrocardiogram signal in accordance with an activity characteristic of the user.

18. The device of claim 17 further comprising a communications port that provides a link between the electrocardiogram device and peripheral devices external to the electrocardiogram device.

19. The device of claim 18 wherein the link is an r.f. link.

20. The device of claim 18 wherein the link is an infrared link.

* * * * *